(12) United States Patent
Eggink et al.

(10) Patent No.: US 6,410,096 B1
(45) Date of Patent: Jun. 25, 2002

(54) METHOD FOR PRODUCING A BIOLOGICALLY DEGRADABLE POLYHYDROXYALKANOATE COATING WITH THE AID OF AN AQUEOUS DISPERSION OF POLYHYDROXYALKANOATE

(75) Inventors: Gerrit Eggink, Ede; Martin Dinant Northolt, Suawoude, both of (NL)

(73) Assignee: Stichting Onderzoek en Ontwikkeling Noord-Nederland (SOONN), Leeuwarden (NL)

( * ) Notice: Subject to any disclaimer, the term of this patent is extended or adjusted under 35 U.S.C. 154(b) by 0 days.

(21) Appl. No.: 09/347,417

(22) Filed: Jul. 6, 1999

Related U.S. Application Data

(62) Division of application No. 08/765,147, filed on Jan. 23, 1997, now Pat. No. 5,958,480.

(30) Foreign Application Priority Data

Jun. 23, 1994 (NL) ................................ 9401037

(51) Int. Cl.[7] .................. B32B 27/00; C08G 63/00; C08G 63/66; B05D 5/00
(52) U.S. Cl. .................. 427/385.5; 528/361; 524/845; 427/372.2; 427/384
(58) Field of Search .................. 426/293, 305, 426/308, 310; 528/361; 427/372.2, 384, 385.5; 428/480, 483; 524/845

(56) References Cited

U.S. PATENT DOCUMENTS 5,685,756 A * 11/1997 Noda ................... 442/327

FOREIGN PATENT DOCUMENTS

| DE | 40 40 158 A1 | * | 6/1992 |
| EP | 0 274 151 A2 | * | 7/1988 |
| WO | WO 91/13207 | * | 9/1991 |
| WO | WO 92/18553 | * | 10/1992 |
| WO | WO 93/11656 | * | 6/1993 |

* cited by examiner

*Primary Examiner*—Vivian Chen
(74) *Attorney, Agent, or Firm*—Young & Thompson

(57) ABSTRACT

A method for producing a biologically degradable polyhydroxyalkanoate coating in the form of an elastomeric film, wherein an aqueous dispersion of polyhydroxyalkanoate or a mixture of polyhydroxyalkanoate is prepared and the dispersion is applied to the surface to be coated, after which water is made or allowed to evaporate to obtain a polyhydroxyalkanoate film, the film formation taking place at a temperature lower than the melting point of the polyhydroxyalkanoate, wherein the polyhydroxyalkanoate is a Pseudomonas polyhydroxyalkanoate other than a polymer or copolymer of β-hydroxyvalerate or β-hydroxybutyrate, without requiring additional steps to render the film elastomeric.

4 Claims, No Drawings

METHOD FOR PRODUCING A BIOLOGICALLY DEGRADABLE POLYHYDROXYALKANOATE COATING WITH THE AID OF AN AQUEOUS DISPERSION OF POLYHYDROXYALKANOATE

CROSS-REFERENCE TO RELATED APPLICATIONS

This application is a division of application Ser. No. 08/765,147, filed Jan. 23, 1997, U.S. Pat. No. 5,958,480.

DESCRIPTION

The present invention relates to a method for producing a biologically degradable polyhydroxyalkanoate coating, wherein an aqueous dispersion of polyhydroxyalkanoate is applied to the surface to be coated. In particular, the invention relates to the coating of surfaces which form part of a product to be supplied for consumption to a human being or animal and/or surfaces which form part of a product which is not resistant to high temperatures. A suitable example of a product to be coated is a foodstuff, in particular cheese. The invention also relates to objects coated with such a polyhydroxyalkanoate coating, and also to elastomeric, films of polyhydroxyalkanoate and latices thereof. Elastomeric means the polyhydroxyalkanoates behave at room temperature as elastomers, wherein the crystals serve as physical crosslinks providing a minimum elongation at break of 50%.

Poly(3-hydroxyalkanoates) (PHA) are biologically degradable polymers which can be accumulated by microorganisms as sources of carbon and energy (Anderson and Dawes 1990, Microbiol. Rev. 54:450–472). Poly(3-hydroxybutyrate) (PHB) and the copolymer poly(3-hydroxybutyrate)co-valerate (PHB/HV) are the most known and best studied forms of PHA and are classified as polyhydroxyalkanoates of the PHB type. In the past ten years, a large number of new types of PHA have been found. In particular, Pseudomonas strains have proved to be capable of synthesizing PHAs with diverse compositions (Lageveen et al. 1987, Appl. Environ. Microbiol. 54, 2924–2932). These polyhydroxyalkanoates comprise 3-hydroxy acids having a carbon-chain length of $C_6$–$C_{14}$ and are termed polyhydroxyalkanoates of the PHA type.

In order to be able to use polyhydroxyalkanoates, they must be derived from biomass and separated from contaminating cell parts such as proteins and lipids. Two important working-up strategies have been developed for PHB and PHB/HV. The first method relates to an extraction with a solvent such as methylene chloride, dichloroethane, chloroform or trichlorobenzene (Lafferty et al. 1988, Biotechnology vol. 6b, 136–176). The disadvantage of this method is that the organic solvents used are toxic and environmentally unacceptable. The use of these solvents would not only make the working-up of PHAs expensive but also considerably limit the number of possible applications of PHAS. All the applications in which PHAs come into contact with products to be applied to or consumed by a human being or animal, such as foodstuffs, are ruled out in this case because small residues of the solvent which is harmful to health can, after all, always be present.

In the second working-up method, the bacteria cells containing PHB/HV are broken open by means of a combined physical, chemical and enzymatic procedure. In this way, the PHB/HV granules are released from the biomass and an aqueous dispersion is produced, viz. a latex. The aqueous PHB/HV dispersion is further purified of cell constituents by means of rinsing steps and centrifugation. A dry PHB/HV powder which can be processed further to produce, for example, foils, small bottles, fibres etc. can then be obtained by means of spray drying the dispersion (Holmes 1985, Phys. Technol. 16, 32–36).

With a view to the environmental requirements, great need has arisen for biologically degradable products. This certainly applies to products which comprise a solid support with a coating. Processing of PHA to form such a coating is an interesting field of application. It is known of PHB and the copolymer PHB/HV that they can be processed in various ways to form a coating. In the first place, by applying a PHB solution in an organic solvent such as chloroform to the surface of the coated agent and allowing the solvent to evaporate. It is clear that this is a very unacceptable method for environmental reasons.

In a second approach, use is made of an aqueous dispersion of PHB, PHB remaining behind as a powder on the surface of the agent to be coated after evaporation of the water. The PHB granules do not fuse and films can only be formed by exposing the surface coated with PHB powder to a solvent such as chloroform (Marchessault et al. 1990, in Novel Biodegradable Microbial Polymers) or by heating the surface coated with PHB powder to the melting point of PHB. This process is disclosed in international patent application WO91/13207 of Marchessault and Lepoutre. Marchessault and Lepoutre describe a method of preparing a coated or impregnated paper or other fibre construct, a latex for use in the preparation of paper or other fibre constructs and films and self supporting films. They describe a latex comprising a colloidal suspension in water of essentially non-crystalline particles of a poly-β-hydroxyalkanoate polymer or copolymer and illustrate butyrate and valerate as preferred hydroxyalkanoates. Their latex will comprise 10 to 50%, preferably 15 to 30%, more preferably 20 to 25% by weight of the PHA. Typically their latex will comprise 10 to 15 parts by weight. They describe that a film can be made from a latex by casting a dilute solution of 15–25% w/w solids on an impervious surface and allowing the water to evaporate slowly at room temperature. They state that heating the air dried film in a drying oven at a temperature 30 degrees below $T_m$ causes moderate fusion. These films have a microporous structure and can be hot pressed at 100–140° C. and 1000–5000 psi to produce flexible translucent films of average to high crystallinity. The hot fusion treating of PHB/V copolymer containing 21% by weight PHV provides water imperviousness. Dense transparent films are formed by exposing air dried films to solvent or liquid vapour atmospheres such as chloroform and other halogenated solvents. Explicitly Marchessault and Lepoutre describe "A few grams of 21% HV polymer latex was diluted to 20–30% w/w solids with distilled water. The resulting mixture was poured on a clean glass surface and allowed to air dry at room temperature overnight. A white uniform coat or film with little or no strength was obtained. It was then placed in a convection oven set at 100° C. for a period of not less than 10 min. A partially fused film was obtained". Hot pressing the resulting film provided a film with at most elongation at break of 30%. Alternatively subjecting the partially fused film to chloroform provided an extremely smooth and tough film.

Disadvantages also apply to these known methods, firstly the use of an organic solvent and secondly, the performance of a heating step in which a temperature above 100° C. has to be used. The applications are therefore also clearly limited in this case. Marchessault and Lepoutre's main application is for impregnating paper. They disclose nothing with regard to preparing elastomeric films. Their coatings are either microporous and non-peelable or thermoplastic exhibiting at most elongation at break of 30%. They do not disclose elastomeric films suitable for appliance to or consumption by humans or animals.

DE-4 040 158 describes how the use of organic solvents is harmful to health and how the presence of the solvent in the coating makes it impossible to use them in the foodstuffs or pharmaceutical industry, in particular as packing material also for material for treating wounds. A further disadvantage mentioned is that the known coatings are available solely as impermeable films. For many applications, however, such as medical bandaging or other materials for absorbing body fluids, a porous coating, in particular a coating permeable to gas and air, is necessary, which materials cannot be obtained with the aid of the coatings with solvents. In DE 4 040 158 a dispersion of polyhydroxybutyrate or polyhydroxyvalerate, or copolymers thereof, in water is described for obtaining such a porous coating. The aqueous dispersions can be prepared by stirring PHA powders or directly in the processing of PHA-forming organisms. The coated objects are prepared, according to DE 4 040 158, by applying the dispersion of PHA to the object and then subsequently drying to remove the dispersing agent. Depending on the drying conditions, a more or less porous coating or an impermeable and continuous coating film can be obtained. The degree of porosity can be controlled by the choice of drying conditions and the granule size of the polymer particle. If a continuous and impermeable coating film is desired, heating is carried out to temperatures at which the coating melts to form a film either during the drying or subsequently to the drying. According to DE 4 040 158, a porous non-film-forming coating is advantageous where gas and air permeability is necessary or desirable, as in the case of medicinal bandaging for wound treatment. A porous coating is obtained by not heating the PHA coating to the melting point so that a film is not formed. In certain cases, sintering in the region of the melting point is advantageous to produce coatings having a defined porosity. The melting point is 173.3° C. for polyhydroxybutyrate and it is 126.6° C. for polyhydroxybutyrate-co-hydroxyvalerate, with a ratio of 80:20 mol %. As examples of surfaces to be coated, mention is made of nonwoven fabric, woven fabric or plastic foil, cellulose, wood, textile fibres, metal or glass.

Various products, in particular food products such as cheese, are coated with a synthetic, non-biologically degradable plastic. The plastic of this rind cannot be recovered or be recycled and presents a problem for the environment. Furthermore, such a coating must fulfil a large number of functions and a large number of requirements. The coatings which have been described above do not fulfil the requirements which are imposed on a cheese coating or a coating for a temperature-sensitive agent. The coating material serves to prevent mechanical damage and also attack by moulds. The coating must offer both mechanical and hygienic protection. Furthermore, the coating must preferably be easy to apply, for example by immersion or coating with a sponge or brush. In particular, in the case of cheese, the coating advantageously affects the lustre and rind formation and it must adhere well to the wet surface of the cheese. In addition, after drying, a coating must be produced which does not crack and does not stick, for example, to boards or other cheeses. The coating should also be semi-permeable since $CO_2$ and certain other flavouring components must be able to diffuse through the coating in order not to adversely affect maturing. Water vapour must also be allowed to pass through in a controlled manner so that natural maturing can occur without any question of excessive weight loss. On the other hand, components must not diffuse into the cheese from the coating. Furthermore, the coating must keep well during prolonged storage, there must be good adhesion to any paraffin layer to be applied and there must be no peeling after vacuum packaging. In addition, the machines which are used must be easy to clean. It will be clear that these properties apply not only to cheese coatings but are generally desirable.

Although biologically degradable and compostable coatings exist, they are generally water-soluble polymers which are consequently also water-sensitive. Examples of these are polyvinyl alcohol, polyethylene oxide, and also proteins such as gelatine. Hitherto, there has been no possible use of polyhydroxyalkanoate films as a coating in the foodstuffs industry, on the one hand, because of the use of organic solvents and, on the other hand, because of the need to heat the polyhydroxyalkanoates to the melting point, which could unnecessarily damage the product.

The object of the present invention is to solve the problems explained above. The present invention relates therefore to a method for producing a biologically degradable poly(3-hydroxyalkanoate) coating in the form of an elastomeric film, in which an aqueous dispersion of poly(3-hydroxyalkanoate) is prepared and the dispersion is applied to the surface to be coated, after which water is made or allowed to evaporate to obtain a film, the film formation taking place at a temperature lower than the melting point of the polyhydroxyalkanoate, and the polyhydroxyalkanoate used being a polymer which is made up of saturated or unsaturated 3-hydroxy fatty acids having a carbon-chain length of 6–14. The 3-hydroxy fatty acids can therefore contain 6, 7, 8, 9, 10, 11, 12, 13 or 14 carbon atoms suitably the method can even be carried out at a temperature more than 35° C. below the melting point.

A method for producing a biologically degradable polyhydroxyalkanoate coating in the form of an elastomeric film, in which an aqueous dispersion of polyhydroxyalkanoate is prepared and the dispersion is applied to the surface to be coated after which the water is made or allowed to evaporate to obtain a film, the film formation taking place at a temperature lower than the melting point of the polyhydroxyalkanoate with a polymer which occurs in Pseudomonas being used as polyhydroxyalkanoate, with the proviso the polyhydroxyalkanoate is not a polymer or copolymer of β-hydroxybutyrate or β-hydroxyvalerate, also forms part of the invention. The method for producing coating in the form of an elastomeric film according to the invention does not require further steps of hot fusion, hot pressing or contact with chloroform or halogenated solvent to obtain the elastomeric characteristic. Selection of specific hydroxyalkanoates as starting material in an aqueous dispersion ensures elastomeric properties are acquired merely upon drying the aqueous dispersion after applying it to the surface to be coated. On the basis of what was known regarding film formation and coatings of polyhydroxybutyrate and polyhydroxyvalerate and copolymers thereof it was totally unexpected that films having an elastomeric character could so simply be obtained. The films according to the state of the art with PHB and PHV required additional measures as described in detail above. Furthermore it could not be predicted that hydroxyalkanoates made up of saturated or unsaturated 3-hydroxy fatty acids having a carbon chain length of 6–14 would be suitable for preparing an aqueous dispersion even having characteristics suitable for use as a coating at all. Such an aqueous dispersion could be expected to have a chewing gum like structure in water or hydrophilic media. It also was not to be expected what the properties of any resulting film would be and certainly not that they would be so fine or so differnt from those of the described PHB and PHV films. Suitably the method according to the invention can be carried out at a temperature more than 35° C. lower than the melting point of the polyhydroxyalkanoate. Preferably, a polymer is used which occurs in fluorescent Pseudomonas belonging to the RNA homology group I. The polymers of PHA occurring in fluorescent Pseudomonas belonging to the RNA homology group I do not, after all, comprise PHB or PHB/HV and have such low melting points, glass transition temperatures and crystallinity that the film formation takes place at a temperature lower than the melting point of the polyhydroxyalkanoates and can even occur at a temperature more than 35° C. below the melting temperature.

PHB and the copolymer PHB/HV, the polyhydroxyalkanoates of the PHB type, are typically thermoplastics having a high melting point (120–180° C.) (Byrom 1987, TIBTECH 5, 246–250). These polymers are highly crystalline. PHAs formed by Pseudomonades, in particular by fluorescent Pseudomonades belonging to the RNA homology group I have, on the other hand, typically elastomeric properties. The melting point of this category of polyhydroxyalkanoates varies between 40 and 60° C. and the crystallinity depends on the composition, but is between 0 and 30% (Marchessault et al. 1990, Ind. J. Biol. Macromol. 12, 158–165). Pseudomonas strains can easily be brought in a known manner to high production levels of PHA (Eggink et al. 1992, Proceedings of ACS Division of Polymeric Material 67, 130–131). Pseudomonas produces no PHB, and therefore, the polyhydroxyalkanoates which are formed by Pseudomonas can be used in an outstanding way in a method according to the present invention without first extracting PHB therefrom. In particular. because the working up of polyhydroxyalkanoates from microorganisms provides an aqueous dispersion, mixtures of polyhydroxyalkanoates occurring in microorganisms, in particular, are extremely suitable for use in a method according to the present invention. The working-up and coating can be performed continuously and in a minimum number of steps. As already stated, the PRA-containing bacteria cells can be broken open by means of a combined physical, chemical and enzymatic procedure, as a result of which the PHA granules are released from the biomass and an aqueous dispersion is produced which can be purified further from contaminating constituents by means of washing steps and centrifugation. With the present method, spray drying of the dispersion and adding of organic solvents are no longer necessary. The processing of PHA to form a coating can be (carried out) just by applying the dispersion as it is obtainable directly by working-up from the microorganisms and by allowing it to dry. The polyhydroxyalkanoates of the PHB type probably do not form an impermeable film because of the high crystallinity and the high glass transition temperature of 0–4° C. the invention in all embodiments (method of preparation, film, coated product, latices) is preferably directed at polyhydroxyalkanoates having a glass transition temperature below 0° C.

In the method according to the invention, a high-temperature step is unnecessary for sintering or melting for the purpose of film formation, in contrast to the method which was known for poly(3-hydroxybutyrate) or poly(3-hydroxybutyrate)-co-valerate coatings. Neither the presence of an organic solvent nor an intermediate step in which the aqueous dispersion of PHA is dried to form a powder and then dissolved in an organic solvent is necessary. With the method according to the present invention, it is therefore possible to coat products which may not be exposed to an excessively high temperature and/or to coat products which are applied to or consumed by a human being or animal and in which organic solvents must not be present. The coating does not per se need, however, to be applied to or consumed by the animal or the human being.

The method according to the present invention can be performed at a temperature in the range of 0–30° C., preferably at a temperature in the range of 10–18° C. The choice of temperature employed will depend on the product to be coated and on economic considerations. The PHA or PHAs used will also be a factor on which the temperature to be used depends.

The method according to the invention can be performed with good results using a dispersion whose dry-matter content of PHA is at least 10%. Outstanding results are achieved with a dry-matter content higher than 30% and even higher than 50%. Dispersions with a dry matter content higher than 65% have been shown to be suitable embodiments for use in preparing elastomeric films according to the invention.

The method in which an aqueous dispersion according to the present invention for coating a product is used has been performed by the inventors with PHAs of the PHB type such as PHB/HV and PHB but these did not yield a film, only a powdered coating whose powder granules exhibited no or little mutual adhesion. The known coating could not be peeled off as a film from the coated product. The coating did not have the mechanical strength of a film. The inventors results agree with what has already been stated in DE 4 040 158 and PCT 91/13207 for PHB and the copolymer of PHB with hydroxyvalerate. A film having good mechanical strength and containing PHB granules can only be formed by exposing the surface coated with PHB powder or aqueous dispersion to a solvent such as chloroform or by heating to the melting point.

Polyhydroxyalkanoates of the PHA type with saturated or unsaturated 3-hydroxy fatty acids having a carbon-chain length between $C_6$ and $C_{14}$ are, inter alia, produced by Pseudomonas strains, in particular fluorescent Pseudomonas strains belonging to the RNA homology group I. This category of hydroxy fatty acids has typically elastomeric properties, with a melting point between 40 and 60° C. and a crystallinity between 0 and 30% (Marchessault et al. 1990, Ind. J. Biol. Macromol. 12, 158–165) and yields outstanding films by the present method. Preferably, the method according to the invention is performed with polyhydroxyalkanoate copolymers which comprise at least 3-hydroxy acids having carbon-chain lengths of $C_8$–$C_{10}$. Outstanding results are obtained if the mixture comprises at least 50% $C_8$–$C_{10}$ PHAs.

An advantage of the use of dispersions is that standard additives such as stabilizers, plasticizers, fillers, dyes, emulsifiers. thickening agents, antioxidants, antistatics, preservatives, crosslinking agents, etc. can be added to the dispersion and the properties of the film can be simply improved and modified thereby. In addition, the presence of the water phase offers the possibility of mixing the PHA with other water-soluble, biologically degradable polymers. Other biologically degradable polymers which can be taken up in the dispersion comprise polyvinyl alcohol, gelatine, methylcellulose, polyethene oxide, pvp, starch. Furthermore, an anti-fungal agent can be taken up in the dispersion.

As stated above, the method according to the present invention can advantageously be used to coat foodstuffs, in particular for coating cheese. The film which is obtained by the present method is outstandingly suitable for coating cheese. All the requirements which are imposed thereon with respect to a suitable cheese coating are fulfilled by the coating which can be obtained by the present invention. In particular, the mechanical strength of the coating is a positive factor. The fact that the PHA granules yield, without heating to the melting point, a film having sufficient mechanical strength to function as cheese coating is very surprising since PHAs of the PHB type yielded only a powdered coating. The film obtained resembles a "latex" film and is easy to distinguish from a coating which is obtained with an aqueous dispersion of the PHB type without the heating step to the melting point of the PHA. In an embodiment which is particularly suitable for producing a coating or film according to the invention, a drying time of less than 24 hours at an atmospheric humidity of 85% and a temperature of 10–18° C. may be adequate. This method according to the invention is outstandingly suitable for producing a cheese coating.

The bacteria cells of Pseudomonas can readily be cultured, the polyhydroxyalkanoates formed depending on the medium on which the Pseudomonas is cultured. Thus, various fatty acids, such as oleic acid and linoleic acid, can be used as hydroxy fatty acids for the PHA to be formed.

Polyhydroxyalkanoates of other microorganisms may, of course, also be used in the method according to the present invention, provided they are saturated or unsaturated 3-hydroxy fatty acids having a carbon-chain length of 6–14. The composition of the polyhydroxyalkanoates may be controlled by choosing the media on which the microorganisms are cultured so that, on the one hand, the presence of PHB and PHB/HV can be avoided in the polyhydroxyalkanoate mixture to be used for the method and, on the other hand, the composition of the polyhydroxyalkanoates produced by a microorganism and, consequently, also the properties of the film can be precisely controlled.

The present invention also relates to a product coated with a polyhydroxyalkanoate film, said film being elastomeric and said film comprising polyhydroxyalkanoate made up of saturated or unsaturated 3-hydroxy fatty acids having a carbon-chain length of 6–14. The invention also comprises a product coated with a polyhydroxyalkanoate film, said film being elastomeric and said film comprising polyhydroxyalkanoate which occurs in Pseudomonas, preferably polyhydroxyalkanoate which occurs in fluorescent Pseudomonas belonging to the RNA homology group I with the proviso the polyhydroxyalkanoate is not a polymer or copolymer of β-hydroxybutyrate or β-hydroxyvalerate. In particular a coated product according to the invention can be a product to be applied to or consumed, by a human being or animal or a product which must not be exposed to 100° C. or more. A suitable product is cheese. The product coated with polyhydroxyalkanoate film may also be composed of a mixture of polyhydroxyalkanoates of the abovementioned type. The invention relates to all products coated with polyhydroxyalkanoate film of the above type which can be prepared by the method according to the invention. The products coated with a polyhydroxyalkanoate according to the invention do not consist of poly(3-hydroxybutyrate) or a copolymer thereof, poly(3-hydroxybutyrate)-co-valerate or poly(3-hydroxyvalerate) since, to prepare such coatings, a heating step is necessary to form a film. Besides this these polymers or copolymers do not provide elastomeric films as is clear from the literature cited above.

The invention furthermore comprises an elastomeric film of polyhydroxyalkanoate in which the polyhydroxyalkanoate is made up of saturated or unsaturated 3-hydroxy fatty acids having a carbon-chain length of 6–14. The invention also comprises an elastomeric film of polyhydroxyalkanoate in which the polyhydroxyalkanoate occurs in Pseudomonas, preferably in fluorescent Pseudomonas belonging to the RNA homology group I with the proviso the polyhydroxyalkanoate is not a polymer or copolymer of β-hydroxybutyrate or β-hydroxyvalerate. Preferably a film according to the invention is water resistant. I n particular, the invention relates to an elastomeric film of polyhydroxyalkanoate which is suitable as a coating for products suitable to be applied to or consumed by human beings and/or animals. The film according to the invention can suitably be applied to hydrophilic surfaces and will exhibit good attachment properties to such a surface without requiring a heating step or any other step than drying at a temperature below $T_m$. In fact temperatures more than 35° C. below $T_m$ can even be applied. Cheese is a suitable product. A preferred film according to the invention will comprise an elongation at break of at least 50%. Suitably the elongation at break will be over 200%. The dry-matter content of a film according to the invention can be more than 10%. Preferably it is higher than 30%, even higher than 50%. Another property of a film which is suitable in particular as cheese coating is a film which contains less than 4.5% of parts which are soluble in water. The typical gas permeability is 3–5 l/m$^2$/hr at a temperature of 20° C. and relative humidity of 90–0% for a film according to the invention. These values being for a film with a thickness of 0.1 mm. Not only is the invention directed at the novel and inventive films but also at latices useful for production of such films as can be produced in the various embodiments of the preparation method of coated products according to the invention.

Thus an aqueous latex-like dispersion of polyhydroxyalkanoate made up of saturated or unsaturated 3-hydroxy fatty acids having a carbon chain length of 6–14 falls within the scope of the invention. Also an aqueous latex-like dispersion of polyhydroxyalkanoate, wherein the polyhydroxyalkanoate occurs in Pseudomonas, preferably polyhydroxyalkanoate which occurs in fluorescent Pseudomonas belonging to the RNA homology group I, with the proviso the polyhydroxyalkanoate is not a polymer or copolymer of β-hydroxybutyrate or β-hydroxyvalerate falls within the scope of protection. Such dispersions preferably having a pH higher than 8, preferably higher than 10. Suitably the pH is 12 as illustrated in the Examples. A dispersion according to the invention may further comprise more than 30%, preferably more than 50%, in particular more than 65% polyhydroxyalkanoate as dry weight. Preferably an aqueous latex-like dispersion according to any of the aforementioned embodiments is substantially free of compounds toxic to a human being or animal. In addition it is substantially free of contaminant cell rests of cells from which the polyhydroxyalkanoate has been derived.

Use of an aqueous latex-like dispersion according to the invention in any of the embodiments described above for preparing a film or product coated with a film comprising drying the aqueous dispersion at a temperature below the $T_m$ and even more than 35° C. below the $T_m$ of the polyhydroxyalkanoate for obtaining an elastomeric film also falls within the scope of the invention.

EXAMPLE 1

Preparation of a PHA Dispersion

The starting point is formed by Pseudomonas cells cultured on oleic acid and containing between 30 and 90%

PHA. The composition of the polymer is 4.4% 3-hydroxyhexanoate, 33.5% 3-hydroxyoctanoate, 32.2% 3-hydroxydecanoate, 14.4% 3-hydroxydodecanoate and 15.5% cis-5,3,3-hydroxytetradecanoate. A suspension is prepared from the biomass which has a dry-matter content of 10% (weight/volume). 1 mg of lysozyme is added per gram of biomass to break up the peptidoglycan layer. Then 0.1 ml of neutrase (NOVO Nordisk, 0.5 AU/g) is added per gram of cells and incubation is carried out for 60 min at 37° C. After that, 0.1 ml of alcalase (NOVO Nordisk) is added per gram of cells and incubation is carried out for 90 min at 55° C. while stirring. Finally, 5 M NaOH solution is added until the pH is 12 and incubation is carried out for 15 min at room temperature. The latex thus produced is washed and concentrated by centrifugation or microfiltration. Scanning electron microscopy reveals that the PHA dispersion is composed of granules which vary in size between 0.4 $\mu$m and 2 $\mu$m. The PHA dispersion is found to be 90 to 99% pure with the aid of gas-chromatographic analysis and elemental analysis. It has been ascertained that in general a pH higher than 8 during working up of the PHA biomass to the latex dispersion improves the working up efficiency.

EXAMPLE 2

Preparation of a PHA Coating on Cheese

The PHA dispersion described in Example 1 can be applied to a cheese surface by brushing or immersion. For a dry-matter content of 20 to 25%, the drying time is approximately 24 hours at a temperature of 12° C. and an atmospheric humidity of 85%. After drying, a dry, smooth, water-resistant film with good adhesion is produced. The elongation at break is approximately 400%. The typical gas permeability is 3–5 l/m$^2$/hr at a temperature of 20° C. and relative humidity of 90–0%. These values being for a film with a thickness of 0.1 mm. This is comparable with that of PHA which is purified with the aid of chloroform.

EXAMPLE 3

Blending PHA with Water-soluble, Biologically Degradable Polymers

The abovementioned water-soluble and biologically degradable polymers can readily be mixed with the PHA when the latter is still in the latex phase. The starting point is formed by the latex mentioned in Example 1 to which said polymers can be added as a solution or as a powder, the powder form preferably taking place in quantities which can dissolve in the aqueous phase of the latex. Thus, PHA and water-soluble polymer can be mixed with one another in any desired ratio. The polymers soluble in the aqueous phase have a favourable effect on the stability and the homogeneity of the latex. The properties of the coating as formed from such a latex can differ appreciably with respect to the pure PHA coating, especially as regards the mechanical and adhesion properties, the gas permeability and the water sensitivity. The differences which can be achieved thereby are within the field of a person skilled in the art and fall within the scope of protection of the present invention.

EXAMPLE 4

Crosslinking of PHA During or After Drying the Latex

Depending on the composition of the substrate, the PHA may contain unsaturated carbon bonds in the side groups. Under the influence of, for example, UV radiation, sulphur or peroxides, these may mutually form crosslinks and thus join chains and parts of chains of the polymer to one another. A number of physical properties of the PHA film formed can be altered by incorporating crosslinks. Solubility and mechanical properties, tackiness, and the prevention of the formation of a crystalline fraction can be controlled in this way. The starting point is formed by a latex which is worked up as in Example 1 with a PHA in which a quantity of monomer containing unsaturated (carbon) bonds is incorporated. Drying produces a film from the latex which then loses its thermoplastic nature under the influence of light, air and/or additions of certain substances to the latex as a result of the formation of crosslinks. The material thereby loses its melting point. The latex can also be modified or blended in the ways mentioned above in Examples 2 and 3.

What is claimed is:

1. Method for producing a biologically degradable polyhydroxyalkanoate coating on a product in the form of an elastomeric film, wherein an aqueous dispersion of polyhydroxyalkanoate or a mixture of polyhydroxyalkanoates is prepared and the dispersion is applied to the surface to be coated, after which water is made or allowed to evaporate to obtain a polyhydroxyalkanoate film, wherein the film formation takes place at a temperature lower than the melting point of the polyhydroxyalkanoate and wherein the polyhydroxyalkanoate used is a polymer which occurs in Pseudomonas, said method of producing an elastomeric film being carried out in absence of further steps of hot fusion, hot pressing or contact with chloroform or halogenated solvents to obtain the elastomeric characteristic with the proviso the polyhydroxyalkanoate is not a polymer or copolymer of $\beta$-hydroxybutyrate or $\beta$-hydroxy-valerate.

2. A method as claimed in claim 1, wherein the film comprises polyhydroxyalkanoate which occurs in fluorescent Pseudomonas belonging to the RNA homology group I.

3. An aqueous dispersion of polyhydroxyalkanoate, wherein the polyhydroxyalkanoate occurs in Pseudomonas, with the proviso the polyhydroxyalkanoate is not a polymer or copolymer of $\beta$-hydroxybutyrate or $\beta$-hydroxyvalerate.

4. An aqueous dispersion according to claim 3, wherein the polyhydroxyalkanoate occurs in fluorescent Pseudomonas belonging to the RNA homology group I.

* * * * *